(12) United States Patent
Debry et al.

(10) Patent No.: US 8,603,388 B2
(45) Date of Patent: Dec. 10, 2013

(54) METHOD FOR OBTAINING A BIOCOMPATIBLE COMPOSITE IMPLANT

(75) Inventors: Christian Debry, Paris (FR); André Walder, L'Hay les Roses (FR)

(73) Assignees: Protip SAS, Lingolsheim (FR); Universite Louis Pasteur (ULP), Strasbourg (FR); Hopitaux Universitaires de Strasbourg (HUS), Strasbourg (FR)

( * ) Notice: Subject to any disclaimer, the term of this patent is extended or adjusted under 35 U.S.C. 154(b) by 1520 days.

(21) Appl. No.: 12/084,244

(22) PCT Filed: Oct. 26, 2006

(86) PCT No.: PCT/FR2006/002410
§ 371 (c)(1),
(2), (4) Date: Apr. 28, 2008

(87) PCT Pub. No.: WO2007/048935
PCT Pub. Date: May 3, 2007

(65) Prior Publication Data
US 2009/0253099 A1    Oct. 8, 2009

(30) Foreign Application Priority Data
Oct. 27, 2005  (FR) ...................... 05 11005

(51) Int. Cl.
*B22F 3/15* (2006.01)
*A61F 2/20* (2006.01)
*A61F 2/28* (2006.01)

(52) U.S. Cl.
USPC ....... 419/2; 419/8; 419/9; 419/52; 623/23.53; 623/23.55; 623/23.72; 623/9

(58) Field of Classification Search
USPC .......... 419/2, 8, 9, 52; 433/174; 623/23.64, 9, 623/23.53, 23.55, 23.72
See application file for complete search history.

(56) References Cited

U.S. PATENT DOCUMENTS

| | | | |
|---|---|---|---|
| 4,374,669 A | | 2/1983 | MacGregor |
| 4,550,448 A | * | 11/1985 | Kenna .......................... 623/23.6 |
| 5,358,522 A | * | 10/1994 | Montgomery et al. .... 623/14.11 |
| 5,855,612 A | | 1/1999 | Ohtuki et al. |
| 6,402,515 B1 | * | 6/2002 | Palti et al. ..................... 433/174 |
| 6,913,623 B1 | * | 7/2005 | Zhu ............................. 623/23.15 |
| 2005/0025656 A1 | * | 2/2005 | Bhaduri et al. ................. 419/52 |

FOREIGN PATENT DOCUMENTS

| | | |
|---|---|---|
| EP | 0 856 299 A1 | 8/1998 |
| JP | 01-275766 A | 11/1989 |
| WO | WO 02/066693 A1 | 8/2002 |

* cited by examiner

*Primary Examiner* — Roy King
*Assistant Examiner* — Ngoclan T Mai
(74) *Attorney, Agent, or Firm* — Buchanan Ingersoll & Rooney PC (57) ABSTRACT

The invention concerns a method for obtaining a metal implant for open porosity tissue support and/or replacement, characterized in that it comprises the following steps: (i) selecting a mould, (ii) arranging in the mould a solid metal core (7), (iii) filling the volume of the mould (1) still available with a powder of microspheres (3), (iv) consolidating the microspheres (3) with each other as well as with said at least one solid core (7) by electrical discharge sintering.

15 Claims, 3 Drawing Sheets

METHOD FOR OBTAINING A BIOCOMPATIBLE COMPOSITE IMPLANT

The present invention relates to the domain of metallic prosthesis that are implantable in man or animal.

The present invention concerns more specifically a method for production of a metal implant implantable in man or animal of which the open porosity enables the colonization by living cells, thus playing the role of a support structure allowing the natural reconstruction of the missing organ following an operation or a traumatic shock.

Particularly, it can be total larynx prosthesis aimed to enable the larynx reconstruction for patients with a laryngectomy, i.e. a total ablation of the larynx following a cancer as an example.

In a more general manner, the domain of the present invention extends to all the prosthesis for local reconstruction relating to a bone wall such as the top of the skull, the mandibles, or the thoracic wall.

More specifically, the present invention concerns a method for the production of a composite implant associating microspheres of titanium or of a titanium-based alloy or of a biocompatible alloy, with pieces of solid titanium or of a titanium-based alloy or of a biocompatible alloy.

It exists today several techniques implementing titanium or titanium-based alloys to obtain biocompatible prosthesis i.e. tolerated and not degraded by the living organism in which they are implanted.

Titanium and titanium-based alloys present indeed the advantage of being light, resistant to the corrosion, thus resistant to the fluids circulating in the living organisms, and moreover, present good mechanical properties.

They enable to consider solid implants, even if they have a consequent size, not very allergenic and not very susceptible to create inflammatory reactions.

All this is known from the prior art.

It can be mentioned, as an example, the use of solid titanium to make hip or knee prosthesis.

Such a device, presents disadvantages inherent to the solid titanium, namely that the structure of its surface does not enable the adhesion nor the colonization by tissues adjacent to the prosthesis. So that once implanted in a living organism, the prosthesis will tend to separate from its living support, osseous or other, after one more or less long period.

More recently inorganic materials based prosthesis, such as hydroxyapatite or glass called bioactive insofar as they show certain capacities to be colonized by living tissues, especially bone tissues, were developed.

However these prosthesis did not present mechanical qualities comparable with the ones made of solid titanium or of a solid titanium based alloy.

The ideal is that the surgeon can have a prosthesis presenting the mechanical qualities of solid titanium or a solid titanium based alloy on one hand, and of bioactivity on the other hand.

It was thus imagined, in the prior art, to realize implants made up of a solid titanium core covered by an hydroxyapatite or a bioactive glass layer.

In addition to its complexity of realization, this device presented moreover defects in the adhesion of the surface layer of the core of the device.

It was however remedied to this new disadvantage by more or less complex methods. By way of non-restrictive examples, the invention described in the patent application JP No 1-275766 can be mentioned. This complex production method enables in particular, after two stages in solution and one stage of heating, to improve the adhesion of the bioactive layer on the solid titanium core.

The method of surface treatment of solid titanium or of titanium-based alloy described by B. Walivaara, I. Lundstrom and P. Tengvall in clinical Materials (Vol. 12, pages 141-148) can also be mentioned. This last method presents however the disadvantage to result only in an extremely fine coating of the core of the implant completely insufficient to enable an effective colonization by tissues.

The patent application U.S. Pat. No. 5,855,612 describing a method of which the objective is to obtain an apatite film at the surface of the core of the prosthesis can also be mentioned. For this, the invention proposes to treat the core of the prosthesis by immersion in an aqueous solution of hydrogen peroxide.

It is nonetheless true that the above-mentioned disadvantages persist and particularly that a rapid and durable tissue colonization can not be obtained in a septic medium.

This default, crippling for the surgeon, can be explained in particular by the fact that the size of the obtained pores, not controllable for any of the above-mentioned methods, these are the microorganisms that are generally pathogenic and of an appropriate size, that are favoured first to lodge themselves in.

The pathogenic microorganisms being of extremely variable size, and the tissues likely to colonize the surface of the prosthesis being of a unique size, it is easy to understand that the competition in the colonization of the surface is only very rarely won by the latter.

From there it follows infections, severe surgical complications and in certain cases, the death of the patient.

Another improvement to the implants of solid titanium or of solid titanium based alloys is proposed in the patent application EP 0 856 299 that describes the resort to the use of microspheres of titanium, of titanium-based alloys or of biocompatible materials, being consolidated to lead to a prosthesis of which the dimensional specifications and the state of the surface are determining to ensure, after implantation of said prosthesis in vivo in a non sterile environment, a cellular or tissue colonization faster than a possible colonization by a pathogenic microorganism.

The porosity is effectively present in the thickness of the structure of the implant and the size of the pores can be predetermined by the choice of the gauge of the used microbeads.

According to the invention described in the patent application EP 0 856 299 such an open porosity metal prosthesis can be submitted to a complete colonization. It is then a rigid structure likely to constitute a real support for the organ to reconstitute accepting an implantation in an environment that is not aseptic because of their open porosity that enables a rapid tissue colonization, the living cells creating between themselves a real network including the microspheres.

If this patent application brings an undeniable advantage indeed, it settles however only partially the problem, namely that these implants have lost a part of their mechanical qualities, especially the flexibility of solid titanium or of solid titanium and/or other biocompatible metals based alloys.

Thus the prosthesis made of microporous titanium and submitted to important forces are likely to break. It is particularly made reference here to dental implants and to mandibles.

Another disadvantage of those prosthesis obtained by heating treatment of microbeads is that the porosity inherent to its structure makes impossible the operations of classical machining such as thread-cutting and tapping thereby prohibiting several embodiments.

It is in particular extremely difficult to imagine embodiments allowing the integration of flanges or of anchoring points allowing the binding of the prosthesis to its environment in vivo.

Moreover, this limitation is worsened by the fact that the qualities of mechanical resistance of the material prohibit, if holes in the prosthesis are bored, to submit them to significant forces and in particular to use them for fixing elements linking the prosthesis to its environment.

Thus the prior art does not present to date any solution to remedy to the whole disadvantages described above.

Finally, the method of obtaining described in the patent application EP 0 856 299 comprises a stage of "electrical discharge sintering" calling upon an important Joule effect that requires an important quantity of surface energy, namely 20 to 80 J/mm$^2$.

The major disadvantage of such a method using an important Joule effect is that the melting of the metal obtained at the contact point of the beads can be excessive. In that case, cracks linked to an excessive dimensional contraction of the piece can be formed perpendicularly to the direction of the current.

This is very clear in the case of thin plates and of tubes for which the ratio surface/volume is high. The cracked piece is of course unusable. The excessive melting of the metal, linked to this method, can go until the complete melting of several microspheres with formation of molten metal drops. These molten metal drops result in a loss of porosity that makes also the implant unsuitable for the use it is intended for. This disadvantage is all the more marked than the size of the beads is reduced.

In addition, such a method calling upon very important quantities of energy, leads to the formation of a welding bead at the contact point between the beads, itself of an important size. An oversizing of the welding bead can opposed to it is thereafter proceeded to a classic sintering operation.

Indeed, such a sintering operation leading to the reinforcement of the welding by migration of atoms from the surface of a particle to another needs to bring up the piece to a temperature that is proportional to the thickness of the considered material.

Practically, a too much thick welding bead can prohibit any later sintering operation insofar as it would suppose that the piece is brought up to a higher temperature than the melting point of the considered metal or at least that such a melting point is exceeded for such-and-such part of the piece. It follows also from this a loss of porosity.

The method described in the application EP 0 856 299 could make difficult a stage of consolidation by later heating treatment, the solidity of the implants made by its implementation must be acquired from the beginning, what makes its development complex. Moreover, the method described in the application EP 0 856 299 using high energies, the electrodes end up very strongly welded at the piece.

It results from this some complexity of the operation of release from the mould, with risks of deterioration of the moulded piece and a certain deterioration of the electrodes. This welding of the electrodes to the implant imposes in any event that the welded parts of the implant are, thereafter, machined in order to present a surface without any apparent default. Such a machining, delicate because operated on a fragile piece, increases its cost.

In addition, when the welding of the electrode of the implant is too much marked, it results in a loss of porosity that makes it unsuitable for its intended use.

As a conclusion, the method described in the patent application EP 0 856 299 presents several disadvantages that make it hardly applicable to some shapes of implants, moreover even when it is applicable, the mechanical resistance of the obtained pieces remains relatively weak.

The present invention intends to overcome the whole disadvantages described and proposes a biocompatible composite implant totally innovating and based on a new inventive concept and, to date, never described or even suggested in the prior art.

Indeed, the first objective of the applicant is to provide a method for realization of implants with perfect mechanical qualities while offering a total biocompatibility thus enabling to limit considerably the breaking risks and the infection risks.

Therefore, the applicant developed a method going against the whole prejudices and the current research that tend to, as described above in the prior art, either to cover the solid titanium with a thin biocompatible layer or to make implants that are porous in their core and obtained by electrical discharge sintering with high energy.

The present invention explores a very different alternative since it considers, for the first time, the use of an implant made up of at least one solid metal core such as for example the titanium, a titanium-based alloy or a biocompatible alloy and an open porosity metallic superstructure obtained by consolidation of the microspheres.

The present invention is on a way that is diametrically opposite to the existing investigations since it is chosen to drown thin elements of solid metal in an important volume of open porosity metal where the prior art proposed to cover the solid metal with a thin bioactive coating.

According to a first embodiment, the present invention consists of a method for obtaining a metal implant for open porosity support and/or replacement of tissue, characterized in that it comprises the following stages:
(i) selecting a mould (1), nonconductive, of suitable shape corresponding to the desired implant,
(ii) arranging in said mould at least one solid metal core (7),
(iii) filling the volume of the mould (1) remaining available with a powder of microspheres (3), and
(iv) consolidating the microspheres (3) with each other as well as with said at least one massive core (7) by electrical discharge sintering, said stage iv) of electrical discharge sintering being realized by discharge of an electrical current, of a predetermined voltage in order to obtain an energy surface density J lower or equal to 10 J/mm$^2$ between on one hand, at least a first electrode (5) at the periphery of the mould (1) and on the other hand, at least a second electrode (5') of opposite polarity and positioned so as a short-circuit is not formed with said at least one solid metal core (7).

By "solid core" it must be understood a piece, such as an insert, substantially solid in its structure, meaning not made of a fitting of elements such as microspheres or fibers having a grain structure or a section that is lower to a millimeter, and made of a metal such as titanium, titanium-based alloy or any other biocompatible alloy. A solid core can however be made of a fitting of titanium threads with a section noticeably equal or superior to a millimeter.

By "microspheres" or "powder of microspheres" it must be understood a powder obtained by spraying with a rotating eletrode ("Powder Metallurgy of Superalloys", G. H. GESSINGER, Butterworths Monigraphs in Materials, pages 29 to 32) or any other equivalent method resulting in spheres with few or no bumps, of a powder made of metallic microspheres of titanium or of titanium-based alloys or of biocompatible alloys with a perfectly spherical geometry, and/or a state of surface that is practically deprived of irregularities such as described in the application EP 0 856 299 A1. Such a method consists of melting, either with an electric arc or with a plasma torch under neutral gas, or with an electron beam under vacuum, the frontal surface of the cylinder in rapid rotation around its axis. The liquid thus formed migrates, under the action of the centrifugal forces of inertia, towards the periphery of the rotating ingot, from where it escapes in the form of droplets that cool and solidify during their flight in the neutral gas of the enclosure.

By "electrode" it must be understood the end of a conductor, preferentially in brass, linked on one hand to one of the poles of the capacitor system generating the electrical discharge, and on the other hand in contact with a metallic part of the implant to be formed such as a whole of microspheres in contact with each other and/or a solid core. An "electrode" means an electrode of a given polarity or a series of electrodes of same polarity.

By "mould of suitable shape" it must be understood a mould reproducing exactly the shape of the piece to be moulded.

By "electrical discharge sintering" it must be understood any operation aiming at welding the microspheres and at least one solid core by discharge of an electrical current towards the piece to be welded. The publication "Preforming using high-voltage electrical discharge", S. T. S. Al-Hassani & T. J. Davies, Powder Metallurgy, 1980 describes a method of electrical discharge sintering.

In the case of a realisation in titanium for the manufacturing of a given shape, the powder of titanium, which has been screened to obtain the desired granulometric fraction, is poured into the mould in non conductive polymer, reproducing exactly the shape of the piece to produce, electrodes having been previously put in appropriate places, preferentially, but not necessarily, in opposition or in almost opposition on both sides of the mould, in contact with the powder or with an element in solid titanium when setting up a core at an end of the piece. The electrodes are linked to the polarities of a stand of capacitors charged under high tension.

By action on a switch, the discharge current of the capacitors crosses the volume of powder. It is obliged to pass by the points of contact between the particles, i.e. by an infinitely small section. It occurs locally, at these points of contact, a heating by Joule effect (V volts=R ohms×I amps and P Watts=R ohms×$I^2$ amps) that, if the intensity of the discharge current is sufficient, can lead to the local melting of the metal or the alloy.

According to this method, the metallic prosthesis present, except for the parts made of solid metal, an open porosity superstructure characterized by interspheroidal spaces presenting a size that is approximately equal to the third of the diameter of the powders.

This porosity is entirely favourable to the colonization by tissue and it is particularly surprising to note that even the interfaces between the parts of the prosthesis made of open porosity metal and the parts made of solid metal present an interlocking by homogenous welding. It may indeed be expected that, the solid metal being a much better conductor than the microspheres of this same metal, some welding defaults may be noticed further to the stage of electrical discharge sintering.

Thus it could have been anticipated that when the current chooses more preferably the solid metal for its passage, the parts of the superstructure of microspheres located laterally to these lines of current would be badly welded or not welded at all, due to an insufficient Joule effect.

On the contrary, it could also have been anticipated effects of melting of microspheres due to a too important Joule effect for the parts of the superstructure made of metal microspheres located in the axis of the lines of current.

The invention goes behind these prejudices and shows that it is possible to obtain a homogenous welding by electrical discharge sintering with a favourable lay out of the metal cores since an appropriate quantity of energy is used. This quantity of energy is preferably of between 1 and 10 $J/mm^2$ and more preferably of between 3 and 8 $J/mm^2$.

The invention brings another solution particularly favourable by proposing to use an end of at least one of the metal cores as an electrode for the method of electrical discharge sintering.

This solution enables to ensure a particularly optimum diffusion of the electrical discharge in the piece to weld. Moreover it avoids the use of at least one classical electrode in contact with the microspheres and saves thereby the disadvantages usually linked to such use as described above.

Indeed, the use of a classical electrode generates important costs linked on one hand, to the maintenance and the replacement of the electrode that is dependant on the intensity of the discharge and, on the other hand, of the machining operations such as grinding and polishing of the surfaces of the implant, molten or blued in their portion facing the electrode.

Even when a solid core is not directly used as an electrode in the meaning that it is not directly linked to the source of energy, it can be used as an intermediate electrode within the piece to weld. In fact these solid cores constitute zones of electric conductibility higher than the zones made of powder of microspheres. These solid cores judiciously laid out, can be used to diffuse in a more homogenous manner the electrical current in the piece to weld. Thus without increasing the quantity of energy, a good quality welding can be obtained in a homogenous manner. Compared to the prior art, the quantities of energy used are divided almost by ten.

By "judiciously layout", it must be understood any layout of the solid cores that enables a homogenous and optimal diffusion of the current in order for it to reach, in the whole piece, the critical value from which the melting occurs at the points of contact. A judicious layout of a given solid core excludes a layout that makes a short-circuit or almost a short-circuit between two electrodes of opposite polarity. On the contrary, a wise layout of a massive core will be obtained when the interface between it and the powder of microspheres will be substantially perpendicular to the lines of circulation of the current between the electrodes of opposite polarity.

The quantity of energy stored in the capacitors is given by the relation: E Joules=½ C farads×$V^2$ volts.

The intensity of the discharge current of the capacitors is proportional to the stored energy, what means that with a stand of capacitors of a given capacity, it is possible to vary the quantity of energy, thus the intensity of the discharge current, by acting on the loading voltage, which in addition intervenes squared, thus led to an important increase of the quantity of energy stored for a voltage increase.

The energy necessary to weld beads with each other depends on the section of passage of the current towards the piece, thus of its size. It depends also of the ohmic resistance of the material, of its melting point and of the size of the particles of the powder. Indeed, for an equivalent section of passage, the smaller the particles are, the more the number of points of contact is high and the more the discharge current is divided between several circuits. It is then necessary to increase the discharge current by an increase of the stored energy to obtain the same result.

Classically, the necessary energy can vary from almost 40 Joules for a small piece to many hundreds, even many thousands of Joules for a large piece. In practice it is necessary to position the electrodes so that the current passes through the smallest possible section, to reduce the necessary energy and, from an industrial point of view, the size of the welding machine.

In the reality the recovered energy does not correspond exactly to the theoretical calculation giving the load of the capacitors, because it can happen losses in the discharge circuit due to different phenomena such as self-induction effects or parasitic resistances. The adaptation of the quantity of energy necessary to obtain a reinforcement of the material is obtained empirically by checking the cohesion of the titanium beads with mechanical tests of crushing. The duration of the discharge is very weak, 5 to 10 μsec (millionth of second), but the intensity of the current that causes the local melting and the welding of the beads is very high, many thousands to many tens of thousands of amperes according to the size of the piece. The exact determination of the electrical parameters is essential to satisfy the need of reproducibility of the pieces.

The temperature reached at the points of contact between the beads is very high; it exceeds the melting point of the titanium (1660° C.) and even causes the vaporisation of a very small quantity of metal, but the brevity of the discharge, the small size of the molten volume and the diffusion of the produced heat in the volume of the beads, make that the average temperature of the piece remains very low, of between 40 to 60° C.

The invention thus proposes as an embodiment that said first electrode (5) and said at least second electrode (5') are positioned in relation to the metal core (7) so as the lines of current formed between these two electrode are not parallel to the microsphere/metal core (7) interface of higher surface.

The invention provides also as an embodiment that said first electrode (5) and said at least one second electrode (5') are positioned in relation to the metal core (7), so as the lines of current formed between these two electrodes are appreciably perpendicular to the microsphere/metal core (7) interface of higher surface.

The invention provides also as an embodiment that an electrode of a given polarity, is arranged so as to come in contact with at least one solid core (7), and the other electrode of an opposite polarity is arranged so as to come in contact with the microspheres.

Figure 11:
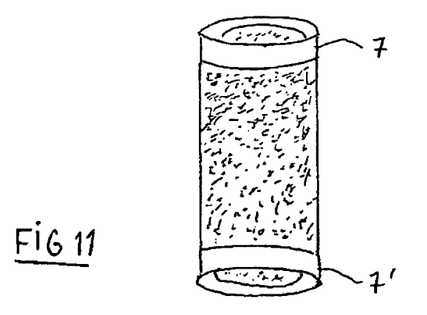
FIG. 11 is a perspective view of a further exemplary embodiment of a trachea prosthesis according to the disclosure.

The invention provides also as an embodiment that an electrode of a given polarity, is arranged so as to come in contact with at least one solid core (7), and the other electrode of an opposite polarity is arranged so as to come in contact with at least another solid core (7'), as shown in FIG. 11.

The optimal diffusion of the current in the implant enables, further to the electrical discharge sintering operation, to obtain between the microspheres on one hand, and between the microspheres and the surface of the cores on the other hand, welding collars of particularly homogenous size. This control of the size of the welding collars enables moreover to consider after the operation of electrical discharge sintering, an operation of sintering in a solid phase, unless the energy necessary to the heating of the pieces and proportional to the size of the collars makes fear that the melting point of the used metal is reached.

This operation of sintering in a solid phase enables to reinforce in an important manner the provided implants and constitutes an undeniable advantage.

Thus, in a preferred embodiment of the invention, the method is supplemented by a stage of sintering in a solid phase where the piece is brought up, in a high vacuum furnace, to a temperature of 1200° C. to 1400° C., preferentially 1250° C. during 3 h to 15 h, preferably 12 h. The sintering operation consists of heating the implant at such a temperature that the powder grains are welding with each other due to atoms displacement in the solid state.

It is important to note that the microspheres being consolidated with each other and to the metal core further to the operation of electrical discharge sintering, the implant can be sintered after having been removed from the mould. This constitutes a significant advantage in comparison with the existing methods, especially the one described in the patent application EP 0 856 299 that requires the use of metallic covers comprising the print of the prosthesis to realize. Indeed, practically the tests showed that covers made of mild steel enable a sintering until 1050° C. due to an eutectic Ti—Fe at 1085° C., a temperature not necessarily leading to a satisfactory linking of microspheres between them. Further to this temperature, it is necessary to use a cover made of titanium that, after sintering, risks to cause problems of separation between the sintered piece and its cover. The present invention beyond the prejudices leading to solve the problem by reducing the sintering temperature, brings an innovative solution that frees itself from the mould by a preliminary reinforcement of the implant enabling on the contrary to increase the temperature of the piece so as to meet the conditions necessary for a solid sintering.

Among the other existing prejudices, it was also to fear that the metal cores complex excessively the operation of moulding, either by creating problems with sealing, or by creating problems with wedging.

However this is not the case. Indeed it is perfectly acceptable in practice to wedge the metal core or the metal cores in the mould by simply compressing the microspheres around said cores.

Thus, the invention provides as a specific embodiment a method comprising an additional stage (ii') between stages (ii) and (iii) which consists of wedging said at least one solid core (7) in the mould (1) with a support element.

By "support element" is must be understood any support element which is biocompatible and known by a skilled man, in particular the titanium and the coral.

According to a specific embodiment of the invention, said support element consists of at least one housing made in at least one of the walls of the mould (1), housing in which at least one of the ends of said at least one solid core (7) comes to fit.

According to another specific embodiment of the invention said support element consists of a powder of microspheres.

Any variation or realization having the same features than the invention must be considered as an equivalent form and thus comprised within the scope of the protection conferred by the present patent application.

According to a particular embodiment the implemented method enables to obtain, with use of a predetermined energy surface density J comprised between 5 to 7 J/mm$^2$, preferentially 6 J/mm$^2$, a dental implant made up of, on one hand of a solid metal core (7) comprising a body presenting at least an external threading (9), eventually of a variable thread, and a head hollowed out in its centre, presenting at least a mean enabling to anchor a tooth, such as an internal thread (11), eventually of a variable thread, and on the other hand a superstructure of microspheres (3) forming a flange placed at the periphery of the head.

According to another embodiment of the invention, the method enables to obtain an implant intended for the replacement of a mandible, made up of on one hand, at least one solid metal core (13, 13') extending in the direction of the length of the implant and comprising at least one fixation mean, such as a hole (17) or an internal thread, and on the other hand a superstructure of microspheres forming the body of the prosthesis (15, 15').

According to an alternative to this embodiment of the invention the obtained implant comprises at least one end of at least one solid metal core that stands out (13, 13') of the superstructure of microspheres (15, 15') so as to facilitate its anchoring by the surgeon.

According to yet another alternative to this embodiment of the invention, the obtained implant presents at least one solid metal core placed at the periphery of its upper edge and that comprises housings of suitable shape, such as internal threads, to receive a dental implantation.

According to another alternative of the invention, the method enables to obtain an implant intended for thyroplasty and comprising a solid metal core forming a base (18) and placed on it, a superstructure made up of microspheres (19), appreciably in the shape of a shark fin.

According to another alternative of the invention, the method enables to obtain an implant intended for the replacement of a trachea, characterized in that it is made up of on one hand at least one solid metal core (19, 19') in the shape of a ring and comprising at least one fixation mean, such as a hole (17') or an internal thread, and on the other hand a superstructure of microspheres forming the body of the prosthesis (20').

These elements will be described in more details below.

These are, of course, non-restrictive examples, the invention enabling extremely varied embodiments.

Any variation or realization showing the features of the invention will have to be considered as an equivalent form and thus as included within the scope of protection conferred by the present patent application.

As tackled above, the object of the present invention is distinguished from prior art in that it realizes an implant that is truly composite.

Such a composite is extremely innovative, as we saw it above, because it goes against the developed efforts to date and because its heterogeneity could have made fear that it cumulates the disadvantages linked to the properties of the two compounds without having the advantages. Thus it could make one fear that the fragility that is inherent to open porosity metals weakens the whole structure, it is however not the case. The solid metal core when it is correctly positioned, of suitable size and section, behaves like a real frame increasing considerably the mechanical properties of the whole implant without decreasing its biodynamical properties.

Figure 1:
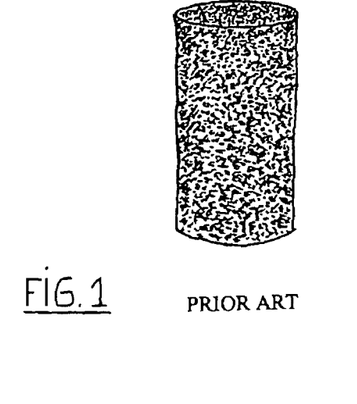
FIG. 1 illustrates a trachea implant without a solid core as known in the prior art.
Figure 2:
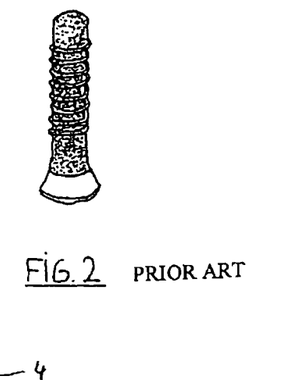
FIG. 2 illustrates a dental implant as known in the prior art, including a screw made of solid titanium and partly covered by a bioactive film.
Figure 3:
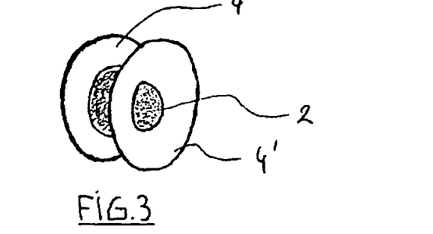
FIG. 3 illustrates an exemplary embodiment of a phonatory implant according to the disclosure.

The invention will be better understood, and its advantages will arise more clearly during the following description of the examples of realization, with reference to the annexed figures wherein:

the FIG. 1 represents an implant of trachea without solid core such as it is known in the prior art, the FIG. 2 represents a dental implant such as it is known in the prior art, meaning a screw made of solid titanium partly covered by a bioactive film, the FIG. 3 represents a phonatory implant realized according to the invention: it is made up of two shoulders (4, 4') holding a cylindrical piece of solid titanium of a diameter of 6 mm and of a length comprised between 4 to 12 mm according to the anatomical features of the patient, tyred with a porous area made up of microspheres (2) of a thickness of almost 1 mm.

During the manufacture of a piece, the sequence of the preparation and filling operations of the mould is as follows:
  positioning of the cylindrical piece of solid titanium into the mould where the electrodes define the limits of the porous area made up of microspheres around the core made up of solid titanium,
  closing of the mould,
  filling of the internal volume of the mould with a powder of microspheres (almost 0.5 g for a length of 8 mm),
  tightening of the unit using adjustment screws to prevent any move and ensure a perfect contact between the different elements,
  connection of each electrode to one of the two polarities of the stand of capacitors and welding by electrical discharge sintering with an energy of 1 200 J that is to say 6 J/mm², the current running radially in the direction of the core of the piece of solid titanium surrounded by the porous area made up of microspheres,
  disassembling of the mould and retrieval of the piece, The piece is then consolidated by sintering under high temperature and under high vacuum. It is then cleaned using ultrasounds in a suitable solvent and then sterilized.

Figure 4:
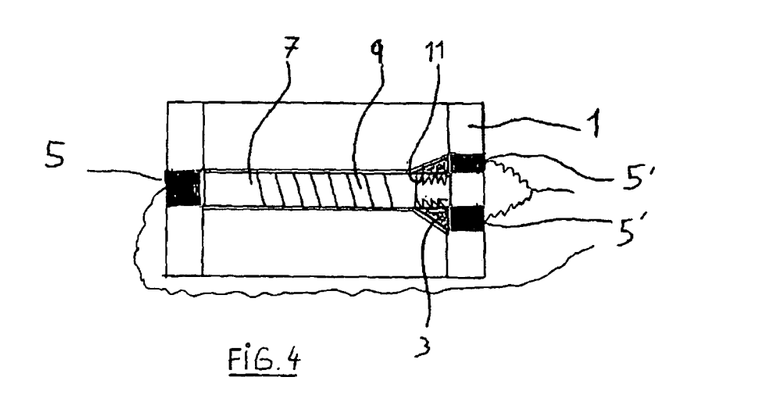
FIG. 4 is a cross-sectional view of an exemplary embodiment of a dental implant according to the disclosure.

The FIG. 4 represents out of a longitudinal section, a dental implant in the shape of a screw (7) in position in its mould (1) realized in a non-conductive material such as Altuglaso®, a first electrode (5) being in contact with the core of the piece made of solid titanium forming the body of the screw (7) and a second pair of electrodes (5') of opposite polarity compared to the first electrode (5) being in contact with the porous part of the head of the screw made up of microshperes (3), the core of the piece (7) forming an intermediate electrode during the electrical discharge sintering.

Figure 5:
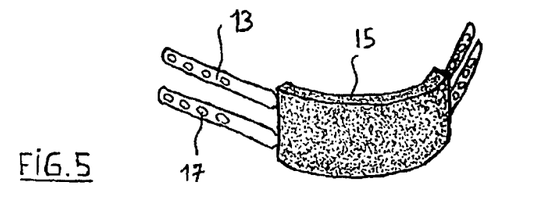
FIG. 5 is a perspective view of an exemplary embodiment of a mandible prosthesis according to the disclosure.

The FIG. 5 represents a mandible prosthesis provided with two cores in the shape of a backing band made of solid titanium (13) which enable the fixing of the implant in the remaining bone of the mandible, for this purpose holes (17) are bored about their ends, apart from the porous area (15) made up of microspheres, for the passage of the screws.

During the manufacture of a piece, the sequence of the preparation and filling operations of the mould is as follows:
  on one of the half of the mould, positioning of the cores maintained in place by screws,
  closing of the mould, set up of the two brass electrodes, filling of the internal volume of the mould where are located the two cores, with a powder of microspheres, as an example 10 g for a mandible of a thickness of 4 mm, of a height of 20 mm and of a total developed length of 45.25 mm, tightening of the unit using adjustment screws to prevent any move and ensure a perfect contact between the different elements, connection of each of the electrodes to one of the two polarities of the stand of capacitors then welding by electrical discharge sintering, the discharge current running perpendicularly to the backing band, the necessary energy being of 1 380 J that is to say 7.6 J/mm$^2$, disassembling of the mould and retrieval of the piece.

The piece is then consolidated by sintering under high temperature and under high vacuum. It is then cleaned by ultrasounds in a suitable solvent and then sterilized.

Figure 6:
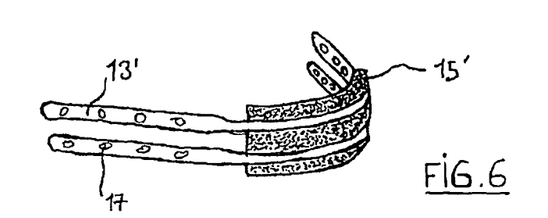
FIG. 6 is a perspective view of a further exemplary embodiment of a mandible prosthesis according to the disclosure.

The FIG. 6 represents an alternative to the prosthesis described in FIG. 5, where the two cores being used as backing bands (13') are of a section enabling their flushing on the external side of the part of the prosthesis made up of microspheres (15'), as an example the thickness of these backing bands, machined in the sheet of titanium, is of 1 mm and their width is of 5 mm; this one can be reduced, as an example to 2.5 mm, in the porous area to increase the volume colonisable by tissues.

Figure 7:
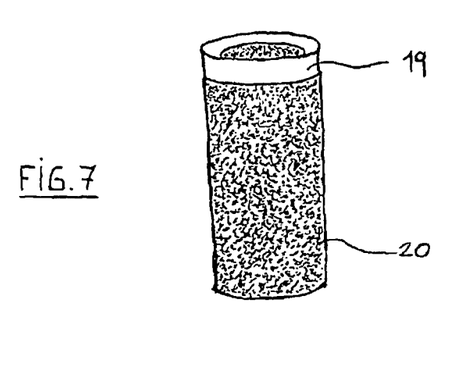
FIG. 7 is a perspective view of an exemplary embodiment of a trachea prosthesis according to the disclosure.

The FIG. 7 represents a trachea prosthesis comprising a solid titanium core forming reinforcement ring (19) and a cylindrical body (20) made up of microspheres, the sequence of the filling operation of the non-conductive mould is as follows, for tracheas of external diameter of 25 mm and of internal diameter of 22 mm positioning of one of the two brass electrodes at one of the end of the mould, the other end being maintained open, installation in contact with the electrode of the end ring in solid titanium (19) forming intermediate electrode, installation of a certain quantity of powder of microspheres, so as to constitute the required height of porous titanium (as an example 1.6 g for a height of 5 mm); levelling with a suitable tool of the surface of powder and packing by vibrations, positioning of the second brass electrode in contact with the powder of microspheres and closing of the mould, tightening of the unit using adjustment screws to prevent any move and ensure a perfect contact between the different elements, connection of each electrode to one of the two polarities of the stand of capacitors then welding by electrical discharge sintering with a total energy of 900 J that is to say almost 6 J/mm$^2$, the current running longitudinally while crossing the different elements of the stacking, disassembling of the mould and retrieval of the piece.

The piece is then consolidated by sintering under high temperature and under high vacuum, then put at length by cutting with a grinding stone. It is then cleaned by ultrasounds in a suitable solvent, then sterilized.

Figure 8:
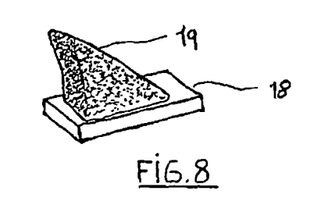
FIG. 8 is a perspective view of a piece of a thyroplasty according to the disclosure.

The FIG. 8 represents a piece of a thyroplasty provided with a solid titanium core forming base (18), and with a superstructure made up of microspheres (19).

During the manufacture of a piece, the sequence of preparation and filling operations of the mould is as follows;

installation of the solid titanium base (18) at the end of the brass electrode in contact with the base of the piece, installation of the electrodes and closing of the mould, filling of the internal volume of the mould with a powder of microspheres (almost 0.5 g), tightening of the unit using adjustment screws to prevent any move and enable a perfect contact between the different elements, connection of each of the electrodes to one of the two polarities of the stand of capacitors then welding by electrical discharge sintering with an energy of 200 J that is to say almost 4 J/mm$^2$, the current running axially, disassembling of the mould and retrieval of the piece.

The piece is then consolidated by sintering under high temperature and under high vacuum. It is then cleaned by ultrasounds in a suitable solvent then sterilized.

Figure 9:
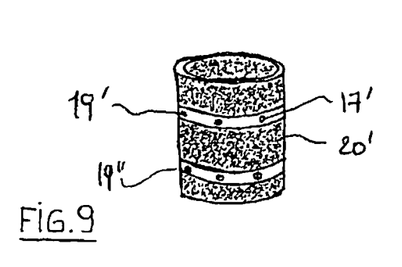
FIG. 9 is a perspective view of a further exemplary embodiment of a trachea prosthesis according to the disclosure.

The FIG. 9 represents a prosthesis of trachea comprising two solid titanium cores forming reinforcement rings (19' and 19") and a cylindrical body (20') made up of microspheres, the sequence of the filling operations of the mould is as follows, for tracheas of external diameter of 25 mm and of internal diameter of 22 mm (thickness of the wall: 1.5 mm):

positioning of one of the two brass electrodes at one of the ends of the non-conductive mould, the other end being maintained open, installation, in contact with the electrode, of a certain quantity of powder, so as to constitute the required height of porous titanium (as an example 3.2 g for a height of 10 mm); levelling with a suitable tool of the surface of powder and packing by vibrations, installation above the powder of a first solid titanium ring (19') forming intermediate electrode, installation of a quantity of powder enabling to obtain the suitable height of porous titanium (as an example 3.8 g for a height of 12 mm); levelling using a suitable tool of the surface of powder and packing by vibrations, installation above the powder of the second solid titanium ring (19") forming intermediate electrode, installation of a certain quantity of powder, so as to constitute the required height of porous titanium (as an example 3.2 g for a height of 10 mm); levelling using a suitable tool of the surface of powder and packing by vibrations, positioning of the second brass electrode in contact with the powder of microspheres and closing of the mould, tightening of the unit using adjustment screws to prevent any move and ensure a perfect contact between the different elements, connection of each of the electrodes to one of the two polarities of the stand of capacitors then welding by electrical discharge sintering with a total energy of 900 J that is to say almost 6 J/mm2, disassembling of the mould and retrieval of the piece.

The piece is then consolidated by sintering under high temperature and under high vacuum, then put at length by cutting with a grinding stone. It is then cleaned by ultrasounds in a suitable solvent then sterilized.

Figure 10:
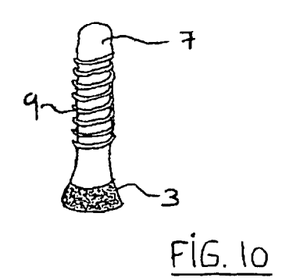
FIG. 10 is a perspective view of an exemplary embodiment of a dental implant according to the disclosure.

The FIG. 10 shows a dental implant made up of a solid titanium core (7) with a cylindrical shape provided with, outside, on one end, a threading (9) intended for being screwed in the bone of the mandible and inside, of an internal thread intended for enabling the fixing of the replacement tooth.

The area made of porous titanium and made up of microspheres (3) will be located at the upper part, above the bone, in contact with the tissues of the gum.

During the manufacture of a piece, the sequence of the preparation and filling operations of the mould is as follows:

positioning of the solid titanium implant (7) forming intermediate electrode in the non-conductive mould and locking of its positioning, installation of the electrodes according to the description made for FIG. 4 and locking of their position, filling of the internal volume of the mould by a powder of microspheres (almost 0.1 g), tightening of the unit using adjustment screws to prevent any move and ensure a perfect contact between the different elements, connection of each of the electrodes to one of the two polarities of the stand of capacitors then welding by electrical discharge sintering with an energy of almost 50 J that is to say 6 J/mm$^2$, the current running longitudinally in the solid titanium implant, disassembling of the mould and retrieval of the piece.

The link of the microspheres with each other and to the solid part is then consolidated by sintering under high temperature and under high vacuum. The piece is then cleaned by ultrasounds in a suitable solvent then sterilized.

Of course, any equivalent to the solid titanium and to the microporous titanium, that is to say presenting similar features, could be envisaged and thus should be considered as equivalent means.

Of course, the different parts of the examples above according to the invention are dimensioned so as to be able to correspond to the morphology of the patient and to present the best required qualities according to the invention, that is to say mechanical and bioactive qualities. The present description consists of a general form of the invention and any modification or obvious improvement, based on the principle of the invention, must be considered as equivalent.

The invention claimed is:

1. A method for obtaining a metal implant for support and/or replacement of tissue comprising at least one solid metal core and at least one open porosity metallic superstructure, said method being characterized in that it comprises the following stages:
   (i) selecting a mould (1), nonconductive, of suitable shape corresponding to the desired implant,
   (ii) arranging in said mould at least one solid metal core (7),
   (iii) filling out the volume of the mould (1) remaining available with a powder of microspheres (3), and
   (iv) consolidating the microspheres (3) with each other as well as with said at least one solid core (7) by electrical discharge sintering,
   said stage iv) of electrical discharge sintering being realized by discharge of an electrical current, of a predetermined voltage in order to obtain an energy surface density J lower or equal to 10 J/mm$^2$ between on one hand, at least a first electrode (5) at the periphery of the mould (1) and on the other hand, at least a second electrode (5') of opposite polarity and positioned so as the lines of current formed between these two electrodes are not parallel to the microspheres/metallic core (7) interface of higher surface.

2. The method according to claim 1, characterized in that said first electrode (5) and said at least second electrode (5') are positioned in relation to the metal core (7), so as the lines of current formed between these two electrodes are appreciably perpendicular to the microsphere/metallic core (7) interface of higher surface.

3. The method according to claim 1, characterized in that an electrode of a given polarity, is arranged so as to come in contact with at least one solid core (7), and the other electrode of opposite polarity is arranged so as to come in contact with the microspheres.

4. The method according to claim 1, characterized in that an electrode, of a given polarity, is arranged so as to come in contact with at least one solid core (7), and the other electrode of opposite polarity is arranged so as to come in contact with at least another solid core (7').

5. The method according to claim 1, characterized in that it comprises an additional stage (ii') between stages (ii) and (iii) consisting of wedging said at least one solid core (7) into the mould (1) with a support element.

6. The method according to claim 5, characterized in that said support element consists of at least one housing made in at least one of the walls of the mould (1), housing in which at least one of the ends of said at least one solid core (7) comes to fit.

7. The method according to claim 5, characterized in that said support element consists of a powder of microspheres.

8. The method according to claim 1, characterized in that it is completed by a stage of sintering in a solid phase so as to reinforce the implant.

9. The method according to claim 1, characterized in that the energy surface density J increases with the size of the implant to realize and is comprised between 3 and 8 J/mm$^2$.

10. The method according to claim 1 for the realization of an implant, characterized in that the energy surface density J is comprised between 5 and 7 J/mm$^2$.

11. An implant for the replacement of a mandible, obtained by implementation of the claim 10, characterized in that it is made up of on one hand, at least one solid metal core (13, 13') extending in the direction of the length of the implant and comprising at least one fixation mean, and on the other hand a superstructure of microspheres forming the body of the prosthesis (15, 15').

12. The implant according to claim 11, characterized in that at least one end of at least one solid metal core stands out (13, 13') of the superstructure of microspheres (15, 15') so as to facilitate its anchoring by the surgeon.

13. An implant for the replacement of a trachea obtained according to claim 10, characterized in that it is made up of on one hand at least one solid metal core (19, 19') in the shape of a ring and comprising at least one fixation mean, and on the other hand a superstructure of microspheres forming the body of the prosthesis (20').

14. The method according to claim 6, characterized in that said support element consists of a powder of microspheres.

15. The method according to claim 10 for the realization of an implant, characterized in that the energy surface density J is 6 J/mm$^2$.

* * * * *